United States Patent
Ng et al.

(10) Patent No.: US 11,839,507 B2
(45) Date of Patent: Dec. 12, 2023

(54) ULTRASOUND SYSTEM AND METHOD FOR CORRELATION BETWEEN ULTRASOUND BREAST IMAGES AND BREAST IMAGES OF OTHER IMAGING MODALITIES

(71) Applicant: KONINKLIJKE PHILIPS N.V., Eindhoven (NL)

(72) Inventors: Gary Cheng-How Ng, Redmond, WA (US); Deborah Kim, Bothell, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 268 days.

(21) Appl. No.: 16/762,515

(22) PCT Filed: Oct. 29, 2018

(86) PCT No.: PCT/EP2018/079531
§ 371 (c)(1),
(2) Date: May 8, 2020

(87) PCT Pub. No.: WO2019/091807
PCT Pub. Date: May 16, 2019

(65) Prior Publication Data
US 2020/0323512 A1    Oct. 15, 2020

Related U.S. Application Data

(60) Provisional application No. 62/582,983, filed on Nov. 8, 2017.

(51) Int. Cl.
*A61B 8/08* (2006.01)
*A61B 8/00* (2006.01)
*A61B 90/00* (2016.01)

(52) U.S. Cl.
CPC ............ *A61B 8/085* (2013.01); *A61B 8/0825* (2013.01); *A61B 8/4245* (2013.01);
(Continued)

(58) Field of Classification Search
USPC ......................................................... 600/437
See application file for complete search history.

(56) References Cited

U.S. PATENT DOCUMENTS

| 6,443,896 B1 | 9/2002 | Detmer |
| 6,530,885 B1 | 3/2003 | Entrekin et al. |

(Continued)

FOREIGN PATENT DOCUMENTS

| EP | 2878266 A1 | 6/2015 |
| EP | 2889743 A1 | 7/2015 |

(Continued)

OTHER PUBLICATIONS

Luo, M., Frisken, S. F., Weis, J. A., Clements, L. W., Unadkat, P., Thompson, R. C., . . . & Miga, M. I. (2017). Retrospective study comparing model-based deformation correction to intraoperative magnetic resonance imaging for image-guided neurosurgery. Journal of Medical Imaging, 4(3), 035003. (Year: 2017).*

(Continued)

*Primary Examiner* — Jason M Ip
*Assistant Examiner* — Renee C Langhals

(57) ABSTRACT

The present disclosure describes ultrasound imaging systems and methods that may be used to assist clinicians in locating lesions during an ultrasound exam that were previously located from images acquired by another imaging system, for example, a magnetic resonance imaging system. A lesion location interface is disclosed that provides visual indications of predicted lesion locations on a display. The predicted lesion locations may be determined by a deformation model included in an ultrasound imaging system as disclosed herein.

19 Claims, 7 Drawing Sheets

(52) U.S. Cl.
CPC ............ *A61B 8/4416* (2013.01); *A61B 8/463* (2013.01); *A61B 8/468* (2013.01); *A61B 8/5223* (2013.01); *A61B 8/5261* (2013.01); *A61B 90/39* (2016.02); *A61B 2090/3954* (2016.02)

(56) References Cited

U.S. PATENT DOCUMENTS

| | | | |
|---|---|---|---|
| 2006/0251301 A1* | 11/2006 | McNamara, Jr. | A61B 8/0825 382/128 |
| 2012/0114213 A1 | 5/2012 | Buelow et al. | |
| 2012/0262460 A1 | 10/2012 | Endo et al. | |
| 2013/0018232 A1* | 1/2013 | D'Souza | A61N 5/1049 600/300 |
| 2013/0063434 A1 | 3/2013 | Miga et al. | |
| 2014/0023254 A1 | 1/2014 | Ishikawa et al. | |
| 2014/0044333 A1 | 2/2014 | Barth et al. | |
| 2014/0343420 A1 | 11/2014 | Zhang et al. | |
| 2015/0011858 A1* | 1/2015 | Caluser | A61B 8/44 600/407 |
| 2015/0150531 A1* | 6/2015 | Futamura | A61B 8/0825 378/37 |
| 2016/0210774 A1* | 7/2016 | Wiskin | A61B 8/483 |
| 2018/0117360 A1* | 5/2018 | Kuwahara | G21K 1/08 |

FOREIGN PATENT DOCUMENTS

| | | |
|---|---|---|
| JP | 2012147939 A | 8/2012 |
| JP | 2016059743 A | 4/2016 |
| WO | 2017060791 A1 | 4/2017 |
| WO | 2017103196 A1 | 6/2017 |

OTHER PUBLICATIONS

Warfield, S. K., Talos, F., Tei, A., Bharatha, A., Nabavi, A., Ferrant, M., . . . & Kikinis, R. (2002). Real-time registration of volumetric brain MRI by biomechanical simulation of deformation during image guided neurosurgery. Computing and Visualization in Science, 5(1), 3-11. (Year: 2002).*

Carter, T., Tanner, C., Beechey-Newman, N., Barratt, D., & Hawkes, D. (Sep. 2008). MR navigated breast surgery: method and initial clinical experience. In International Conference on Medical Image Computing and Computer-Assisted Intervention (pp. 356-363). Springer, Berlin, Heidelberg. (Year: 2008).*

Eiben et al: "Biomechanically Guided Prone-to-Supine Image Registration MRI Using an Estiamted Reference State";2013 IEEE 10th International Symposium on Biomedical Imaging: From Nano to Micro, San Francisco, CA Apr. 2013, pp. 214-217.

Eiben et al: "Breast Deformation Modelling:Comparison of Methods to Obtain a Patient Specific Unloaded Configuration"; SPIE Medical Imaging, 2014, vol. 9036, pp. 903615-1-903615-8.

PCT/EP2018/079531 ISR & WO, Jan. 7, 2019, 15 Page Document.

* cited by examiner

ULTRASOUND SYSTEM AND METHOD FOR CORRELATION BETWEEN ULTRASOUND BREAST IMAGES AND BREAST IMAGES OF OTHER IMAGING MODALITIES

CROSS-REFERENCE TO PRIOR APPLICATIONS

This application is the U.S. National Phase application under 35 U.S.C. § 371 of International Application No. PCT/EP2018/079531, filed on Oct. 29, 2018, which claims the benefit of U.S. Provisional Patent Application No. 62/582,983, filed on Nov. 8, 2017. These applications are hereby incorporated by reference herein.

BACKGROUND

The present disclosure relates generally to correlating images from two or more different medical imaging systems such as magnetic resonance (MR) imaging and ultrasound imaging systems. MR breast imaging may be used for screening and diagnostics purposes such as to identify the presence of and/or quantify parameters associated with a tumor in a tissue of a subject. MR breast imaging is more common in high risk patients, such as those with a prior history of breast cancer and/or certain BRCA2 mutations. MR breast imaging is highly sensitive and may provide for earlier detection than traditional x-ray mammography in some patients. However, the high sensitivity of MR imaging may lead to false positives. Typically, a follow-up ultrasound is performed after a positive result from an MR scan prior to commencement of treatment. Ultrasound may be used to confirm the lesions from MR images, characterize lesions, and/or guide a biopsy of a lesion found in the MR scan.

MR breast imaging is typically performed with the patient prone (i.e. lying face down) with the breast(s) unsupported. In contrast, ultrasound exams are typically performed with the patient supine (i.e. lying face up) with the arm on the side being scanned raised overhead. The different patient positions used for MR and ultrasound may lead to anatomical structures having different appearances between images from the two systems. The shape and/or positions of lesions may also shift due to the different positions of the breast between the two imaging systems. These differences may result in difficulty in finding a lesion noted in an MR image during an ultrasound exam. Large breast size and/or multiple lesions may exacerbate these difficulties. Thus, tools for locating lesions found in an MR scan during a subsequent ultrasound exam may be desired. For example, the ability to and/or confidence in correlating an MR finding in subsequent ultrasound imaging may facilitate an ultrasound guided breast exam in lieu of a more costly in-gantry MR guided breast exam or even obviating subsequent exams in the event that the finding is characterized as benign based on the findings from the ultrasound exam.

SUMMARY

Ultrasound imaging systems and methods that may improve correlation between ultrasound breast images and breast images acquired by other modalities are described.

An example ultrasound imaging system according to principles of the disclosure may include a user interface comprising a display and a user input device, a memory operatively coupled to the user interface, and a processor operatively connected to the user interface and the memory. The memory may include processor-executable instructions, which when executed by the processor may cause the user interface to provide a visual indication of a predicted lesion location, e.g., for guiding image data acquisition using ultrasound imaging, and may further cause the user interface to display an ultrasound image acquired by the ultrasound imaging system. In some embodiments, the memory may include processor-executable instructions for receiving an indication of a suspected location of a lesion in relation to previously acquired image data using a first imaging modality (e.g., an MR image data set), and generating a predicted location of the lesion when the lesion is imaged using a different modality (e.g., ultrasound).

An example method according to principles of the disclosure may include receiving previously acquired image data including information about suspected lesion location(s), applying a deformation model to the previously acquired image data to generate a predicted lesion location, and providing the predicted lesion locations to a lesion location interface. In some embodiments, a method may include receiving imaging data acquired by imaging tissue using a first modality (e.g., MR volume data set), receiving an indication of a suspected location of a lesion within the imaged tissue, applying a deformation model to the suspected location of the lesion to generate a predicted location of the lesion when imaging the tissue using a second modality, and providing a graphical representation of the predicted location on a lesion location interface associated with an imaging system operable to image via the second modality.

An example non-transitory computer-readable medium according to principles of the disclosure may include processor-executable instructions for predicting lesion locations on an ultrasound imaging system, which when executed may cause the ultrasound imaging system to: apply a deformation model to a previously acquired image, display a predicted lesion location, acquire a live ultrasound image, and display the live ultrasound image.

Aspects of the present disclosure, such as certain elements of the user interfaces and/or methods described herein may be embodied in computer-readable media comprising processor-executable instructions. For example, a memory including processor-executable instructions for performing any of the methods described may be included in an ultrasound imaging system according to the present disclosure. In some embodiments, processor-executable instructions for providing one or more graphical user interfaces or elements thereof may be incorporated into a software package for execution on an analysis workstation. Aspects of the present disclosure may facilitate offline review and analysis of ultrasound images as described further below, however it will be understood that the principles described herein may be equally applied to online image review analysis (e.g., analysis performed on the ultrasound system during or shortly after image acquisition).

DETAILED DESCRIPTION

Figure 1:
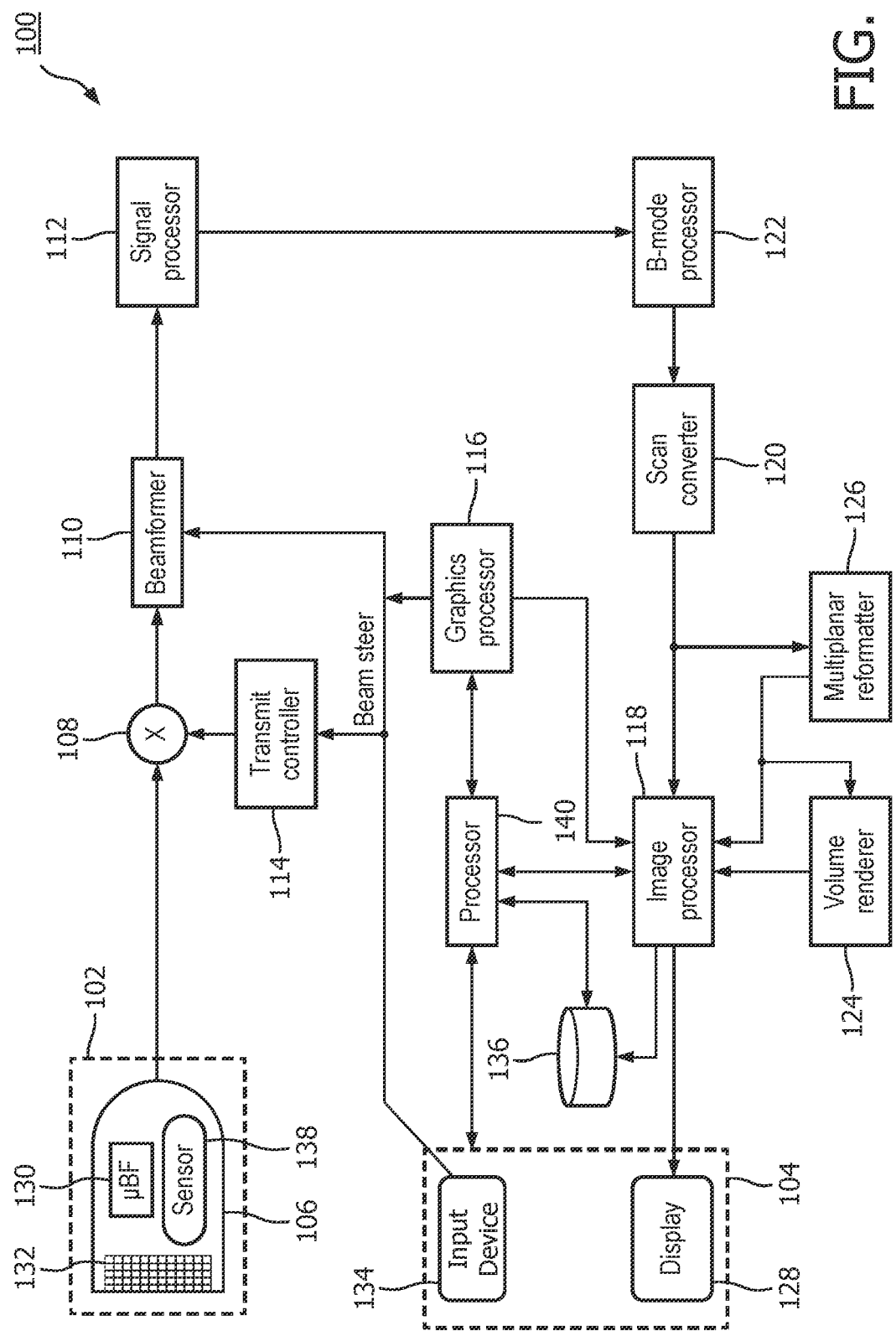
FIG. 1 shows an ultrasound imaging system 100 constructed in accordance with the principles of the present disclosure in block diagram form.

The following description of certain exemplary embodiments is merely exemplary in nature and is in no way intended to limit the disclosure or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Patients, especially those considered high risk for breast cancer, may have their breasts imaged by magnetic resonance (MR) imaging. Although MR is highly sensitive and may provide early detection of breast cancer, MR may be prone to false positives. Accordingly, after a lesion is detected by MR, patients often receive a follow-up ultrasound exam. The ultrasound exam may include imaging the lesion, characterizing the lesion (e.g., size, tissue stiffness, blood flow), and/or performing a guided biopsy of the lesion (e.g., needle biopsy).

A clinician performing the follow-up ultrasound exam is often not the same clinician that performed the MR scan or analyzed the images. The clinician may receive a patient's MR images and/or report from a radiologist that analyzed the MR images. Based on visual inspection of the images and/or interpretation of the report, the clinician must then attempt to find the same lesion or lesions in the patient's breast as were found in the MR image to correlate the findings.

MR breast imaging and ultrasound imaging are performed with the patient in different positions. MR breast scans are typically performed with the patient prone (i.e. lying face down) with the breast(s) unsupported. This may allow gravity to extend the breast tissue for better MR imaging. In contrast, ultrasound exams are typically performed with the patient supine (i.e. lying face up) with the arm on the side being scanned raised overhead to stretch out the breast tissue while allowing an ultrasound probe to make adequate acoustic contact with the breast. Due to the different positions of the patient, the breast tissue may be exposed to different compressive and stretching forces, which may change the shape and/or location of tissues of the breast. Additionally, pressure applied by the probe on the tissue may further displace the breast tissue which may further contribute to the problem of correlating imaging data between two different modalities. The differences in deformation of the breast between one modality (e.g., MR imaging) and second modality (e.g., ultrasound imaging) may make it difficult for the clinician to locate the lesion noted in image from the first modality (e.g., an MR image) during imaging via the other modality (e.g., during the ultrasound exam). For example, the lesion may take a different shape, be obscured by another tissue structure, and/or appear in another location within the breast. Anatomical landmarks (e.g., nipple, areola) may also change in appearance and/or their relative location to the lesion may change. Furthermore, ultrasound and MR are prone to different imaging artifacts, which may hinder lesion location. For example, ultrasound images may include shadowing from Cooper's ligaments, which is not encountered in MR imaging. In some situations, to avoid artifacts obscuring a lesion, a clinician performing an ultrasound exam may have to image a lesion from an angle that corresponds to a different view of the breast than the MR image.

Currently, clinicians manually search for lesions with freehand scanning during ultrasound exams. A large scan volume of breast tissue and/or a large number of scan angles may be required to locate the lesion. The time to locate lesions may be significant, especially if the breast is large and/or there are multiple lesions to be located. The experience of the clinician may also be a factor in the time required to locate lesions during the ultrasound exam. Even when the clinician finds a lesion during the ultrasound exam, the clinician may not be confident that the lesion found during the ultrasound exam corresponds to the lesion found in the MR image.

As described herein, when performing a follow-up ultrasound exam, the ultrasound system may receive imaging data from one modality (e.g., one or more MR volume data sets). The imaging data or portions thereof (e.g., an MR volume data set or a subset of images from the data set) may be loaded into the ultrasound imaging system prior to the ultrasound exam. The lesions of interest may already have been marked in the MR data sets. Lesion markings in the MR data set may have been made by the clinician on the ultrasound imaging system or the MR data set may have been marked (e.g., to identify lesions of interest) prior to loading the MR data set on the ultrasound imaging system. The ultrasound imaging system may include a breast deformation model, which may simulate how a breast imaged with MR will be deformed (e.g., shape, location) during an ultrasound exam. The deformation model may analyze the MR imaging data and predict where noted lesions in the MR data set may be located in a breast during an ultrasound exam.

The ultrasound imaging system may further include a graphical user interface (e.g., lesion location interface) that may provide a visual indication (e.g., graphical representation) of the breast, which may interchangeably be referred to as breast mark, and predicted locations of lesions during the ultrasound exam based, at least in part, on the MR imaging data, as adjusted by the deformation model. The graphical representation may direct the clinician to a location in the breast to scan for locating a lesion of interest marked in the MR data set. The guidance provided by the lesion location interface, the operation of which may be enhanced by the deformation model, may reduce the time required to locate lesions during an ultrasound exam and/or may increase a clinician's confidence that the same lesion was located in the ultrasound exam as was noted in the corresponding MR image.

Although the examples provided herein describe analyzing MR breast images for subsequent ultrasound exams, the principles of the disclosure may be applied to analyzing x-ray mammography images and images of other breast imaging modalities (e.g., 3D breast tomosynthesis). For example, in x-ray mammography, the images are typically acquired while the patient is standing and the breast is compressed between two plates. The deformation model of an ultrasound imaging system may be applied to the resulting x-ray images and the resulting predicted location of a lesion may be provided by a lesion location interface to a clinician performing the ultrasound exam.

An ultrasound imaging system as described herein may include a user interface comprising a display and a user input device, a memory operatively coupled to the user interface, and a processor operatively connected to the user interface and the memory. The memory may comprise processor-executable instructions, which when executed by the processor cause the user interface to provide a visual indication of a predicted lesion location (e.g., a body mark overlaid with an annotation) and display an ultrasound image acquired by the ultrasound imaging system. The memory may further comprise processor-executable instructions, which when executed by the processor cause the processor to apply a deformation model to a previously acquired image to determine the predicted lesion location and provide the predicted lesion location to the user interface. The user interface may also receive an actual lesion location from the user input device and provide a visual indication of the actual lesion location. To further assist the clinician, the user interface may provide a visual indication of at least one of a suggested position (e.g., a distance and angle of an ultrasound probe with respect to some anatomical landmark like the nipple), and/or provide a visual indication of at least one of a current position of the ultrasound probe. In addition to the ultrasound images acquired by the clinician during the ultrasound exam, the user interface may display a previously acquired image (e.g., an MR image).

Referring now to FIG. 1, an ultrasound imaging system 100 constructed in accordance with the principles of the present disclosure is shown in block diagram form. The ultrasound imaging system 100 may be used to implement, at least in part, any of the ultrasound imaging systems described herein. FIG. 1 shows ultrasound imaging system 100, which includes ultrasound probe 102, transducer array 132, microbeamformer 130, transmit/receive (T/R) switch 108, beamformer 110, transmit controller 114, signal processor 112, B-mode processor 122, scan converter 120, multiplanar reformatter 126, volume renderer 124, image processor 118, graphics processor 116, user interface 104, input device 134, and output device 128. The components shown in FIG. 1 are merely illustrative, and other variations, including eliminating components, combining components, rearranging components, and substituting components are all contemplated.

In the ultrasound imaging system 100 in FIG. 1, the ultrasound probe 106 includes a transducer array 132 for transmitting ultrasonic waves and receiving echo information. A variety of transducer arrays are well known in the art, e.g., linear arrays, convex arrays or phased arrays. The transducer array 132 for example, can include a two dimensional array of transducer elements capable of scanning in both elevation and azimuth dimensions for 2D and/or 3D imaging. The transducer array 132 may in some cases be coupled to a microbeamformer 130, typically located in the ultrasound probe 106, which controls transmission and reception of signals by the transducer elements in the array. In the example shown in FIG. 1, the microbeamformer 130 is coupled, such as by a probe cable or wirelessly, to a transmit/receive T/R switch 108, which switches between transmission and reception. The T/R switch 108 may thus protect the beamformer 110 from high energy transmit signals. In some embodiments, the T/R switch 108 and other elements of the system can be included in the transducer probe rather than in a separate ultrasound system base.

The transmission of ultrasonic beams from the transducer array 132, under control of the microbeamformer 130 if present in the particular embodiment, is directed by the transmit controller 114 coupled to the T/R switch 108 and the beamformer 110. The transmit controller 114 receives input from the user's operation of an input device 134 of user interface 104. The input device 134 may be implemented using a control panel (e.g., a touch screen, a console, or a combination of the two) which may include soft and/or hard controls. One of the functions controlled by the transmit controller 114 is the direction in which beams are steered. Beams may be steered straight ahead from (orthogonal to) the transducer array, or at different angles for a wider field of view. In embodiments which include a microbeamformer, the partially beamformed signals produced by the microbeamformer 130 are coupled to a beamformer 110 where partially beamformed signals from individual patches of transducer elements are combined into a fully beamformed signal. In other embodiments, signals from the array 132 are transmitted to the beamformer 110 which forms beamformed signals responsive to the signals from the array.

The beamformed signals may be coupled to a signal processor 112. The signal processor 112 can process the received echo signals in various ways, such as bandpass filtering, decimation, I and Q component separation, and harmonic signal separation. The signal processor 112 may also perform additional signal enhancement such as speckle reduction, signal compounding, and noise elimination. The processed signals may be coupled to a B-mode processor 122, which can employ amplitude detection for the imaging of structures in the body. The signals produced by the B-mode processor may be coupled to a scan converter 30 and a multiplanar reformatter 126 in cases where 3D data is acquired. The scan converter 120 arranges the echo signals in the spatial relationship from which they were received in a desired image format. For instance, the scan converter 120 may arrange the echo signal into a two dimensional (2D) sector-shaped format, or a pyramidal three dimensional (3D) image. The multiplanar reformatter 126 can convert echoes which are received from points in a common plane in a volumetric region of the body into an ultrasonic image of that plane, as described in U.S. Pat. No. 6,443,896 (Detmer). A volume renderer 124 converts the echo signals of a 3D data set into a projected 3D image as viewed from a given reference point, e.g., as described in U.S. Pat. No. 6,530,885 (Entrekin et al.) The 2D or 3D images may be coupled from the scan converter 120, multiplanar reformatter 126, and volume renderer 124 to an image processor 118 for further enhancement, buffering and temporary storage for display on an output device 128. The output device 128 may include a display device implemented using a variety of known display technologies, such as LCD, LED, OLED, or plasma display technology.

The graphics processor 116 can generate graphic overlays for display with the ultrasound images. These graphic overlays can contain, e.g., standard identifying information such as patient name, date and time of the image, imaging parameters, and the like. The graphics processor may receive input, such as a typed patient name, from the input device 134. The input device 134 may include one or more mechanical controls, such as buttons, dials, a trackball, a physical keyboard, and others, which may also be referred to herein as hard controls. Alternatively or additionally, the input device 134 may include one or more soft controls, such as buttons, menus, soft keyboard, and other user interface control elements implemented for example using touch-sensitive technology (e.g., resistive, capacitive, or optical touch screens). To that end, the ultrasound imaging system 100 may include a user interface processor (i.e., processor 140), which may control operations of the user interface such as functions associated with soft controls. One or more of the user controls may be co-located on a control panel. For example one or more of the mechanical controls may be provided on a console and/or one or more soft controls may be co-located on a touch screen, which may be attached to or integral with the console.

The ultrasound images and associated graphics overlays may be stored in memory 136, for example for off-line analysis. In some embodiments, the memory 136 may include local memory provided in the ultrasound system base. In some embodiments, the memory 136 may include a storage device of a picture archiving and communication system (PACS). In some embodiments, ultrasound images and associated data may be stored both locally and remotely on a PACS server. As described herein, the memory 136 may store images acquired from other imaging systems. For example, the memory 136 may store images acquired by another ultrasound imaging system, a magnetic resonance imaging system, and/or an x-ray mammography system.

In addition, the memory 136 may store processor-executable instructions including instructions for performing functions associated with the user interface 104. The user interface 104 can also be coupled to the multiplanar reformatter 126 for selection and control of a display of multiple multiplanar reformatted (MPR) images. As described herein, the memory 136 may store process-executable instructions including instructions for performing functions associated with a tissue deformation model. In some embodiments, the memory 136 may include multiple memories.

In some embodiments, functionality of two or more of the processing components (e.g., beamformer 110, signal processor 112, B-mode processor 122, scan converter 120, multiplanar reformatter 126, volume renderer 124, image processor 118, graphics processor 116, processor 140, etc.) may be combined into a single processing unit or divided between multiple processing units. For example, processor 140 may include two processors: a user interface processor and a deformation model processor. In another example, the graphics processor 116 and the image processor 118 may be combined into a single processor.

In accordance with the principles of the present disclosure, a sensor 138 may be attached to the ultrasound probe 106 and may be operatively associated with a position tracking system 106 (e.g., an electromagnetic (EM) tracking system), such that the spatial location of the probe can be tracked and/or recorded. The processor 140 may be configured to register the ultrasound probe 106 relative to the subject and determine the spatial location of the probe with respect to a subject based on the registration as well as position data received form the position tracking system 102. The processor may be further configured to associate position data with images acquired with the position tracked probe.

In accordance with the principles of the present disclosure, the processor 140 may be configured and/or further configured to receive images and/or data associated with images acquired by another imaging system, such as those stored in memory 136. The processor 140 may be configured to apply a tissue deformation model, based at least in part on the received images and/or data to generate predicted locations of objects (e.g., lesions, anatomical landmarks) within the tissue. The processor 140 may provide the predicted locations to the image processor 124, the graphics processor 116, memory 136, and/or user interface 104.

The processor 140 may receive instructions for the deformation model from memory 136. In some embodiments, the processor 140 may receive additional data from a user (e.g., clinician) via user input device 134. For example, a user may provide data regarding dimensions (e.g., breast width, volume) and/or tissue composition (e.g., fat, glandular, muscle). In some embodiments, the processor 140 may apply a segmentation model to the received images to determine tissue composition and/or dimensions. In another example, a user may indicate the location of lesions in the images acquired by another imaging system. In a further example, a user may indicate a type of deformation model to apply (e.g., supine to prone, compressed to uncompressed).

An example of a tissue deformation model that may be used to implement the tissue deformation model in some embodiments is described in U.S. patent application Ser. No. 13/666,600 "Apparatus and methods of compensating for organ deformation of internal structures to images, and applications of same" (Miga, et al.). The tissue deformation model may be a breast deformation model in some embodiments. An example of a breast deformation model that may be used to implement the tissue deformation model is described in U.S. patent application Ser. No. 14/000,068 "System and method for providing registration between breast shapes before and during surgery" (Barth, et al). Additional examples of breast deformation models that may be used in some embodiments are described in "Breast Deformation Modelling: Comparison of Methods to Obtain a Patient Specific Unloaded Configuration," Eiben, B., et al., *Medical Imaging* 2014: *Image-Guided Procedures, Robotic Interventions, and Modeling*, Proc. Of SPIE Vol. 9036, 903615 and "Biomechanically Guided Prone-to-Supine Image Registration of Breast MRI Using an Estimated Reference State," Eiben, B., et al., 2013 *IEEE 10th International Symposium on Biomedical Imaging: From Nano to Macro*, San Francisco, CA, USA, Apr. 7-11, 2013. These tissue deformation models are provided for example purposes only. Principles of the present disclosure are not limited to the cited examples.

Figure 2:
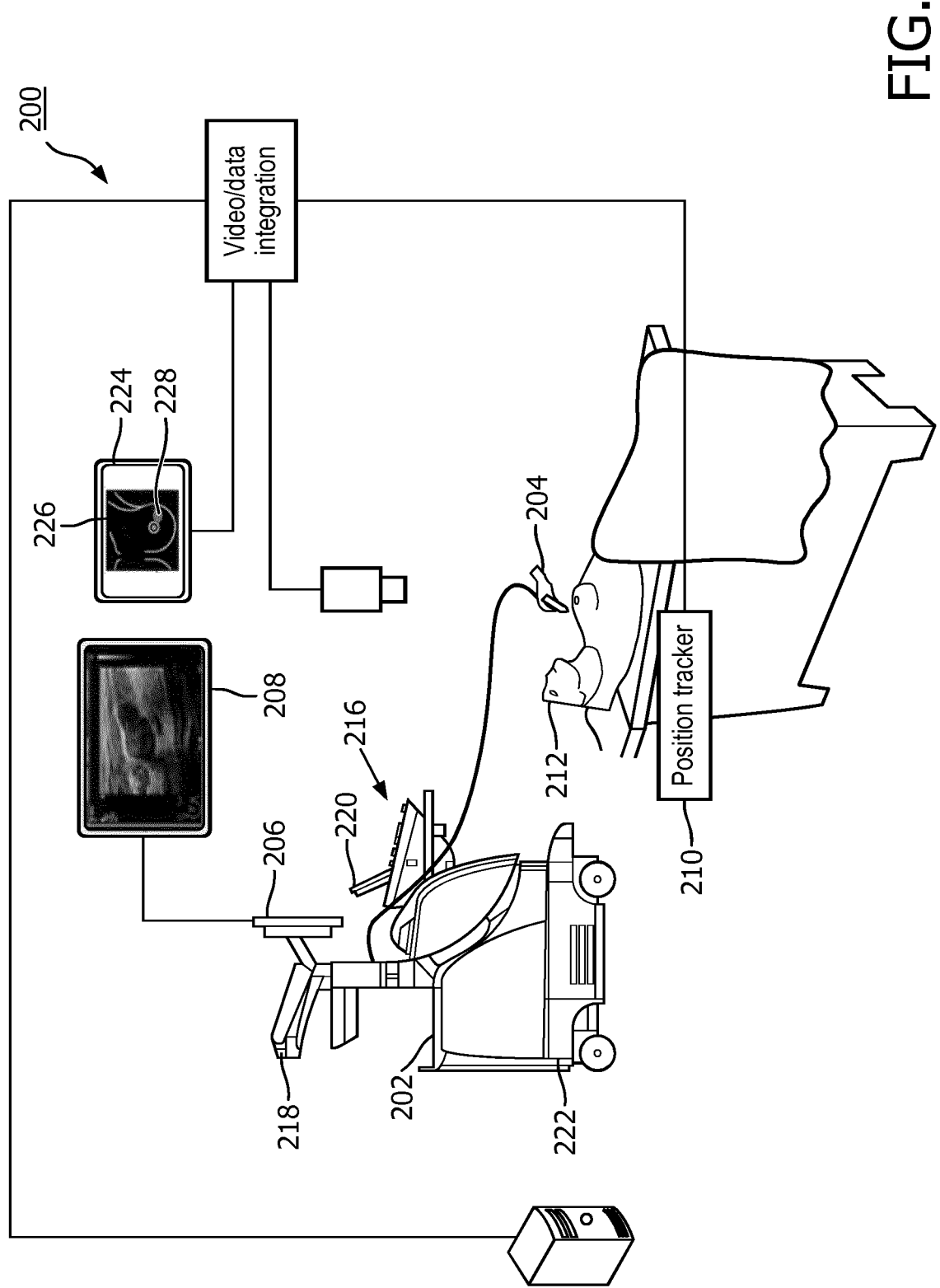
FIG. 2 shows an illustration of an ultrasound imaging system which may be used for breast imaging in accordance with principles of the present disclosure.

FIG. 2 shows an illustration of an ultrasound imaging system which may be used for breast imaging in accordance with principles of the present disclosure. FIG. 2 shows ultrasound imaging system 200, ultrasound imaging device 202, probe 204, display 206, live image 208, position tracking system 210, patient 212, user interface 216, articulating arm 218, touch screen 220, base 222, and lesion location interface 224. The components shown in FIG. 2 are merely illustrative and other variations, including eliminating components, combining components, rearranging components, and substituting components are all contemplated.

The ultrasound imaging system 200 may include one or more of the components of the ultrasound imaging system 100 in FIG. 1. The ultrasound imaging system 200 may include an ultrasound imaging device 202, which may be a cart-based ultrasound imaging device, a handheld imaging device, or other portable imaging device. For example, one or more of the processing components of the ultrasound imaging device 202 (e.g., beamformer, memory, signal processor, B-mode processor, scan converter, multiplanar reformatter, volume renderer, image processor, graphics processor, and/or other processors which may control various operations of the ultrasound imaging device) may be provided in a base 222, which may be a mobile base. The ultrasound imaging system 200 may include a display 206. The display 206 may be attached to the base 222 via an articulating arm 218 for re-positioning the display 206 such as to allow a displayed image to be viewable by others (e.g., the patient, another ultrasound clinician, or a clinician).

The ultrasound imaging device 202 may be connected to a probe 204 via wired (e.g., cable) or wireless (e.g., Wi-Fi) connection. The probe 204 may be used scan breast tissue of a subject (e.g., patient 212). The probe 204 may be configured for freehand operation. By freehand, it is generally meant that the probe is handled (e.g., moved) by a clinician (e.g., ultrasound technician, radiologist) rather than by a machine-controlled actuator. Operation of the probe 204 may be controlled, in part, via the user interface 216. The user interface 216 may include input components, such as mechanical and soft controls, and output components, such as visual, audible and tactile feedback devices. One or more components of the user interface 216 may be implemented using graphical user interface (GUI) elements which may be provided on the display 206, the touch screen 220, or combinations thereof. For example, images (e.g., live image 208) acquired with the probe 204 may be displayed on display 206, on the touch screen 220, or both. Images previously acquired by the ultrasound imaging system 200 and/or another imaging system (e.g., MR imaging system) may be provided on display 206, touch screen 220, or both. The previously acquired images may be displayed concurrently with the live image 208 in some embodiments. The user interface may be configured to provide GUI elements for controlling operations of the ultrasound system. For example, one or more GUI controls may be provided on the touch screen 220.

The user interface 216 may include a lesion location interface 224. The lesion location interface 224 may provide one or more user interface elements to aid a clinician in locating a lesion previously found in an image from a different imaging system (e.g., MR system). One or more of the elements of the lesion location interface 224 may be implemented as GUI elements, which may be provided on the display 206, the touch screen 220, or a combination thereof. One or more elements of the lesion location interface 224 may be provided in one or more interface windows, concurrently or at different times.

The lesion location interface may include location controls, which may include GUI controls provided on touch screen 220, examples of which will be described further below. In some embodiments, such as on a conventional workstation, the location controls may be implemented using GUI controls responsive to conventional input devices such as a mouse, trackball, touch pad, keyboard, and the like. The location controls may enable a user to provide an indication of a suspected lesion location relative to the previously acquired image data (e.g., the imaging data acquired using a first modality such as MR), which suspected location may then be used to generate a predicted location of the lesion when ultrasonically scanning the tissue. The predicted lesion location may be generated based on a deformation model which takes into account the difference in patient positioning of the two imaging modalities. The predicted lesion location may be used to guide the subsequent ultrasound scan, e.g., by providing a graphical representation of the predicted lesion location on an anatomically representative graphic of the lesion location interface 224. The lesion location interface 224 may include graphics which may be displayed on a display of the ultrasound system, on a display of a workstation, or another display. The graphics may be configured to display information (e.g., one or more markings, which may be indicative of a predicted lesion location) in an anatomically intelligent manner, for example by displaying markings 228 on or next to an anatomically representative graphic 226 (also referred to as a body mark). An anatomically representative graphic 226 may include a two-dimensional or a three-dimensional rendering of the anatomical part or organ. In the present context, anatomically intelligent may alternatively or additionally refer to the automatic placement of markings 228 on an anatomically representative graphic, which marking may be indicative of a predicted location of a lesion based on the indicated suspected location of the legion in the previously acquired data set, as adjusted by the deformation model. As described, the image data may be acquired with a position tracked probe, thus, anatomically intelligent may alternatively or additionally refer to the automatic placement of markings 228 on a body mark 226 based the probe's position during acquisition of a particular image (e.g., a graphic indicative of the current position and/or angle of the probe in relation to anatomy, a suggested position and/or angle of the probe, and/or combination of the two). In the illustrated example, the anatomically representative graphic 226 may be a breast graphic illustrating a breast side corresponding to the imaged breast. The breast graphic may be overlaid with one or more markings 228, as will be further described. Markings 228 may also be placed next to (e.g., above, below or on any side of the body mark). The markings 228 (e.g., symbols and/or indicators) may include alphanumeric symbols and/or geometric shapes. In some embodiments, the graphic 226 may not be anatomically representative and may instead be in the form of a clock diagram, with the markings overlaid or provided adjacent to the clock diagram.

The ultrasound imaging system 200 may be operatively associated with a position tracking system 210. The position tracking system 210 may be an electromagnetic (EM) tracking system. An EM tracking system typically includes an EM field generator and a sensor. The sensor may be attached to the probe 204 (e.g., embedded in or externally to the housing of the probe 204). In some embodiments, a tabletop EM field generator may be used. The EM field generator may be movable with respect to a support surface supporting the subject (e.g., an examination table) and thus with respect to the patient. This may enable re-positioning of the EM field generator such that the EM field encompasses the organ or tissue to be scanned (e.g., left breast, right breast). In some embodiments, the EM field generator may be fixed with respect to the support surface. In other embodiments, a different type of position tracking system may be used, such as an optical tracking system (e.g., video, infrared).

Imaging data acquired with a position tracked probe may enable a processor of ultrasound imaging system 200 to determine relative positions of objects within the ultrasound images generated therefrom. For example, the processor of ultrasound imaging system 200 may estimate the spatial location of the probe with respect to the patient 212 using position data from the position tracking system 210, which position data may then facilitate extraction of relevant information from the images acquired with the position tracked probe (e.g., probe 204). For example, ultrasound imaging system may correlate the images acquired with the position tracked probe with images acquired by another imaging system and/or images acquired during a previous ultrasound exam. The probe position data may include position information about the probe such as the position and orientation of the probe in 3D space. The ultrasound imaging system 200 may enable the user to register the probe 204 with respect to the patient's anatomy. For example, the ultrasound imaging system 200 may be configured to associate the spatial location of the probe when placed at relevant anatomical landmarks (e.g., nipple of the breast, boundaries of the breast, etc.) with the respective landmark.

As described, the ultrasound imaging device 202 may receive images acquired from another imaging system, such as an MR system. The received images may be stored in a memory included with the ultrasound imaging device 202. In some embodiments, the received images and/or ultrasound images acquired by the ultrasound imaging system 200 may be stored in single or multi-frame image files in accordance with a standard format (e.g., DICOM format) appended with the corresponding lesion location and/or probe position data. In some embodiments, the lesion location may, for example, be noted using clock angle, distance from the nipple, and depth from the skin line. In some embodiments, the clinician may view the received images on display 206 and/or touch screen 220 and add markings via the user interface 216 indicating lesion location information in the received images. In some embodiments, the clinician may further indicate the tissue type and/or composition on the image. For example, the clinician may manually segment out different regions of the received images from the other imaging system, in order to indicate the tissue type and/or composition.

The received image data from the prior modality, which in some cases may include information indicative of suspected lesion location markings, may be provided to a processor included with the ultrasound imaging device 202. The processor may apply a tissue deformation model to the received image data to determine one or more predicted lesion locations. The predicted lesion locations may be provided to the clinician via the lesion location interface 224, for example, via a graphic indicating highest likelihood position of the lesion 228 on the body mark 226. In some embodiments, the processor may also determine a suggested placement of the probe in relation to the anatomy (e.g., a position and/or angle of ultrasound probe 204 in relation to the nipple or other anatomical landmark) for ultrasonically imaging the lesions.

The ultrasound imaging system 200 may concurrently display the lesion location interface 224, the imported images or data sets from the other imaging modality, and/or the live ultrasound image 208. A clinician may save and/or annotate acquired ultrasound images during the exam. The user can also continue to mark different lesions on the imported data (for example, from MR) during the exam. In some embodiments, an image from the prior acquired image data is concurrently displayed such as to enable the user to mark suspected lesion locations, which locations are then used to generated predicted lesion locations for the second imaging modality (in this case, ultrasound). The additional markings to the received image may be used by the processor to revise the predicted lesion location, and the revised prediction may be updated on the lesion location interface 224.

When a lesion is located with the ultrasound probe 204, the clinician may annotate the ultrasound image with the actual location of the lesion. If the actual location of the lesion differs from the predicted location, the lesion prediction graphic within the lesion location interface 224 may be updated to indicate the actual location of the lesion. In some embodiments, the actual location and predicted location of the lesion may be displayed concurrently by the lesion location interface 224. This may provide the clinician with an estimate as to how possibly inaccurate predicted locations of additional lesions to be located may be. In some embodiments, the actual location of the lesion may be provided to the processor. The processor may use the difference between the predicted and actual lesion locations to adaptively modify the deformation model, which may improve accuracy of the deformation model.

Once a lesion is located during the ultrasound exam, the clinician may measure its dimensions and/or other properties (e.g., stiffness). These additional measurements may be displayed on screen and stored with an image and/or set of images (e.g., cineloop). The clinician may also use the ultrasound imaging system 200 to guide a biopsy of the lesion. The ultrasound images, associated measurements and/or lesion positions (e.g., actual lesion locations, predicted lesion locations) may be stored in a memory of the ultrasound imaging system 200. The images and/or annotations may be stored automatically by the ultrasound imaging system and/or responsive to input by the clinician. The ultrasound images and/or annotations may be reviewed after the ultrasound exam.

In accordance with principles of the present disclosure, the user interface (e.g., user interface 216) of the ultrasound imaging system may be configured to provide a visual indication of predicted lesion locations based on the predicted lesion locations determined by a deformation model. The predicted lesion locations may have been determined based, at least in part, on markings of lesion locations in images acquired by another imaging system. In some embodiments, the visual indication of predicted lesion locations may be provided by displaying a body mark overlaid with relevant lesion location information (e.g., one or more location indicators, annotations, or other). In some embodiments, the body mark may be overlaid with a suggested ultrasound probe location and/or angle or a line representing the actual position of the ultrasound probe based on location tracking.

Figure 3:
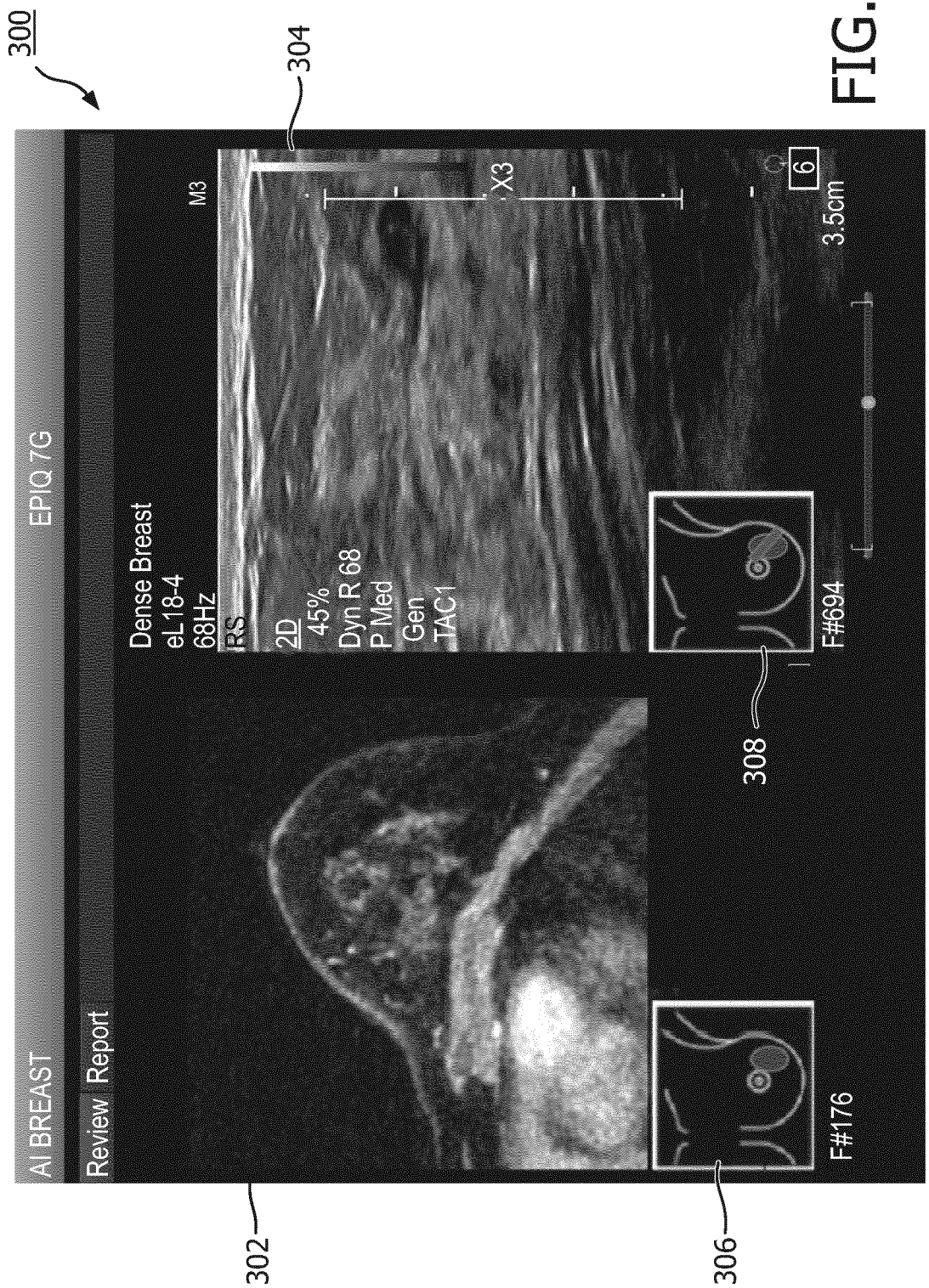
FIG. 3 shows user interface elements associated with a lesion location interface 300 in accordance with principles of the present disclosure.
Figure 4:
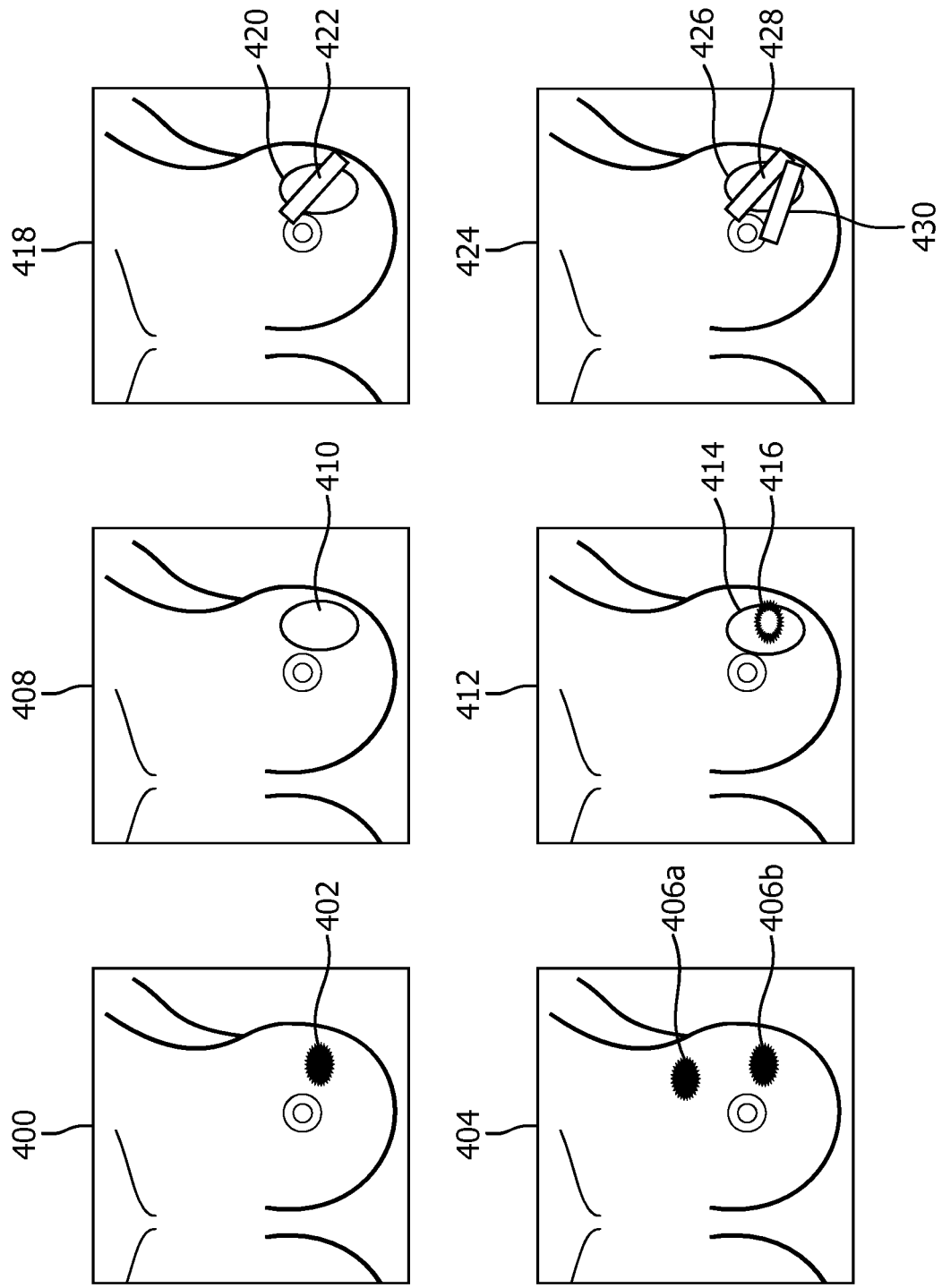
FIG. 4 shows body marks and associated annotations in accordance with principles of the present disclosure.

With reference now also to FIGS. 3 and 4, examples of user interface elements in accordance with the principles of the present disclosure are further described. The user interface may be configured to provide a lesion location interface which may include one or more user interface elements for locating lesions, acquiring and/or annotating breast ultrasound images, and/or marking lesion positions on images received from another imaging system. For example, the lesion location interface may be configured to display a body mark, which in the case of breast ultrasound may be a breast graphic. The breast graphic may provide an illustration of the corresponding breast side that is being imaged and/or characterized, e.g., a right breast graphic may be displayed when imaging or characterizing a right breast and a left breast graphic may be displayed when imaging or characterizing a left breast. The body mark may be overlaid with relevant lesion location information, such as one or more indicators associated with individual predicted and/or actual lesion locations or regions of one or more predicted lesion locations.

FIG. 3 shows user interface elements associated with a lesion location interface 300 in accordance with principles of the present disclosure. FIG. 3 shows lesion location interface 300, received image 302, live image 304, body marks 306 and 308, respectively. One or more of the elements of the lesion location interface 300 may be displayed on a display of an ultrasound imaging system, such as display 206. One or more of the elements of the lesion location interface 300 may additionally or alternatively be displayed on a touch screen, such as touch screen 220 of ultrasound imaging system 200. Elements of the lesion location interface 300 may be provided concurrently or in sequence and may be arranged in one or more interface windows. Additionally, although not shown in FIG. 3, the lesion location interface 300 may provide one or more user controls, such as layout, graphics, and annotate buttons, which may be provided, for example, on touch screen 220 of the ultrasound imaging system 200. The specific examples or arrangement of user interface elements is illustrative only and other embodiments (e.g., hard vs. soft controls) or arrangements of the elements may be employed without departing from the scope of the present disclosure. One or more of the elements of lesion location interface 300 may be used to implement the lesion location interface 224 in the example in FIG. 2.

Received image 302 may be an image from another imaging system that includes the lesion the clinician is searching for during the ultrasound exam. In some embodiments, the received image 302 is a single slice from a volume data set acquired from the breast in another modality. The user can manually scroll through the different slices in the volume data set until the desired slice is displayed. At that point, the user can indicate where on the slice the lesion of interest is. In other embodiments, when the volume data is partially registered to the live ultrasound image, the received image 302 can be an image from a set of received images (e.g., slices of a volume) that corresponds to a location in the tissue that the clinician is currently imaging with the ultrasound imaging system. That is, the location tracking in the ultrasound probe may determine where in the tissue the live image 304 is acquired from. The location may be provided to a processor, and the processor may retrieve the corresponding received image 302 for display.

Body mark 306 may include an annotation that indicates on the anatomy the predicted location of the lesion. In the example shown in FIG. 3, a shaded ellipsoid indicates a region of the breast where the lesion is predicted to be located. Providing the clinician with a predicted location may reduce the volume to be interrogated during the ultrasound and/or the time required to locate the lesion. In some embodiments, not shown in FIG. 3, body mark 306 may include an additional indicator to suggest a position and/or angle of the ultrasound probe for locating the lesion.

Live image 304 may be an image currently being acquired by an ultrasound probe. In some embodiments, live image 304 may be replaced by an ultrasound image saved by the clinician. For example, a clinician may acquire an ultrasound image or images and pause the exam to add annotations to the acquired image. Annotations may include marking the actual location of the lesion, dimensions of the lesion, and/or other properties of the lesion (e.g., stiffness). The image and/or annotations may be stored in a memory of the ultrasound imaging system for later review. After acquiring and/or annotating the image, the clinician may return to acquiring live images or end the exam.

Body mark 308 may include an annotation that indicates where on the anatomy the predicted location of the lesion is located, similar to body mark 306. In some embodiments, as shown in FIG. 3, body mark 308 may include an additional graphic that indicates the current position and/or angle of the ultrasound probe. In some embodiments, only body mark 306 or 308 is presented.

When multiple lesions are to be located during an ultrasound exam, the lesion location interface 300 may provide visual indications of predicted locations for all the lesions to be located. Alternatively, the lesion location interface 300 may provide a predicted location for a single lesion at a time. The clinician may toggle between predicted locations of the multiple lesions. In some embodiments, the lesion location interface 300 may provide an indication of which lesion of a set of lesions is currently being located by the clinician (e.g., 1 of 2, 3 of 4). This may reduce the chance of the clinician ending the exam prior to all lesions being located. When an actual location of a lesion is annotated by the clinician, the lesion location interface 300 may automatically associate the actual location with a particular lesion from the received image and/or the clinician may manually indicate which lesion from the received image the actual location is associated with.

FIG. 4 shows body marks and associated annotations in accordance with principles of the present disclosure. Body mark 400 includes annotation 402 which indicates a predicted location of a lesion. Similarly, body mark 404 includes annotations 406a and 406b, which indicate predicted locations of multiple lesions. Although annotations 402, 406a, and 406b are shown as circles, other annotations may be used (e.g., X's, squares, numbers). Body mark 408 includes annotation 410, which is a shaded ellipsoid of a region where one or more predicted locations of lesions are located. Body mark 412 includes annotations 414 and 416, which indicate a predicted location and an actual location of a lesion within the region, respectively. The actual location may have been added by a clinician via a user input device of an ultrasound imaging system. Although annotations 410 and 414 are shown as ellipsoids, other regional indicators may be used (e.g., quadrant, radial segment). Body mark 418 includes annotation 420 which indicates a region where one or more predicted locations of lesions are located and annotation 422 which indicates a suggested probe location for visualizing the lesion. Body mark 424 also includes annotations 426 and 428 which indicate a region where one or more predicted locations of lesions are located and a suggested ultrasound probe location for visualizing the lesion, respectively. Additionally, body mark 424 includes annotation 430, which indicates a current position of the ultrasound probe. The current position may be provided by a probe tracking system as described herein. Annotation 430 may be updated on body mark 424 as a clinician moves the ultrasound probe. The body marks and annotations shown in FIG. 4 are provided for example purposes only. Other types of annotations and/or combinations of annotations may be provided. In some embodiments, a clinician may choose what annotations are provided on the body mark via a user interface.

An ultrasound imaging system as described herein may apply a deformation model to a previously acquired image, display a predicted lesion location, acquire a live ultrasound image, and display the live ultrasound image. The ultrasound imaging system may display the previously acquired image. During an exam, the ultrasound imaging system may receive an actual lesion location from a user input device and display the actual lesion location to a clinician performing the exam. The actual lesion location and the live ultrasound image associated with the actual lesion location may be stored in the ultrasound imaging system. This may be done in response to an input by the clinician or may be automatic in some embodiments.

An ultrasound imaging system may perform one or more methods as described herein. For example, a method performed by at least a portion of the ultrasound imaging system (e.g., a processor) may include receiving an annotated image (e.g., an MR volume with a marked lesion location), receiving a deformation model type (e.g., supine to prone), applying the deformation model to the annotated image to generate a predicted lesion location, and providing the predicted lesion locations to a lesion location interface (e.g., lesion location interface 224).

Figure 5:
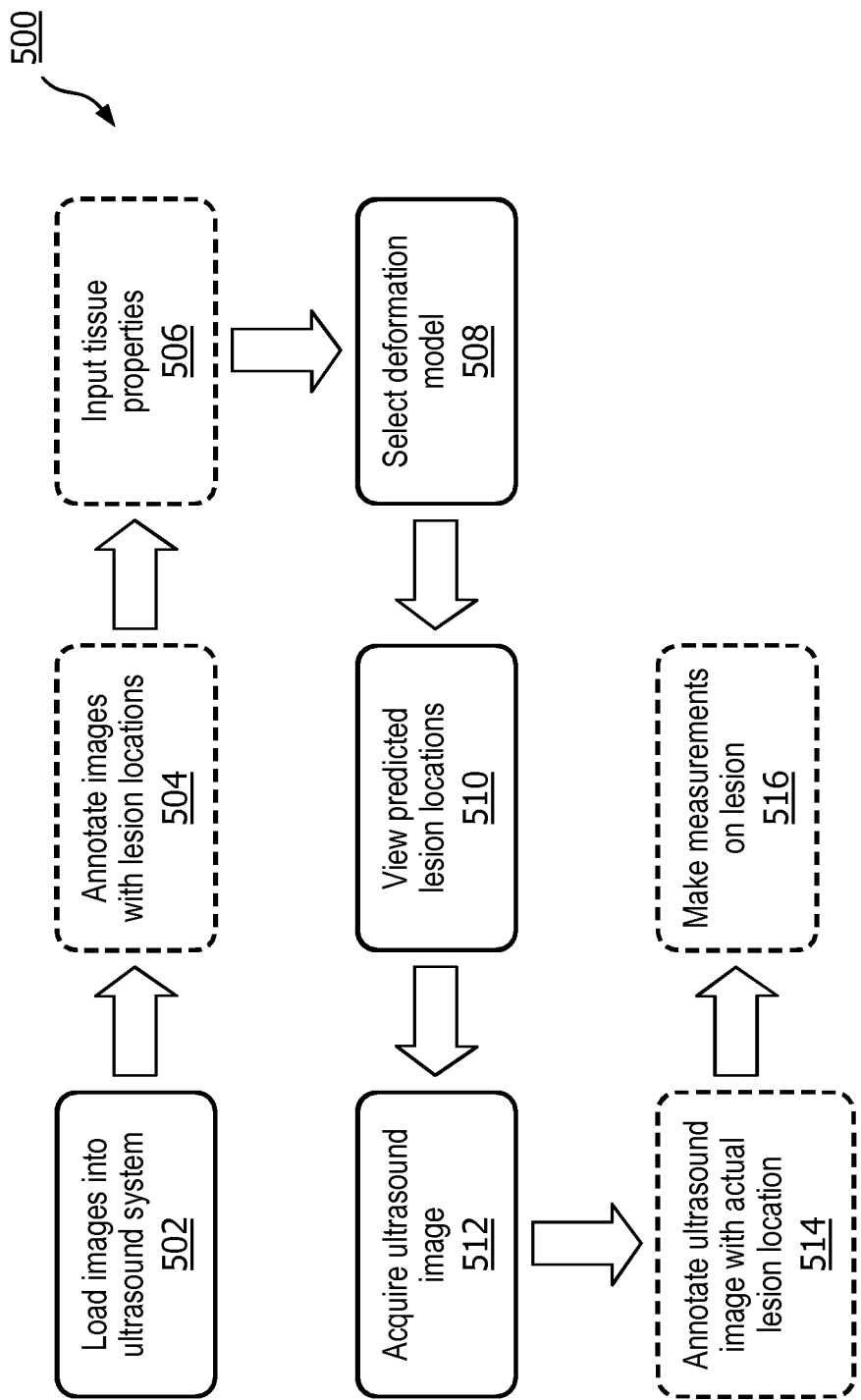
FIG. 5 is a flowchart of an example process for locating lesions noted in previously acquired images in a current ultrasound exam in accordance with principles of the present disclosure.

FIG. 5 is a flowchart 500 of an example process for locating lesions noted in previously acquired images in a current ultrasound exam in accordance with principles of the present disclosure. At Step 502, a clinician may load previously acquired images into an ultrasound imaging system (e.g., ultrasound imaging system 100 or ultrasound imaging system 200). The previously acquired images may have been acquired by an MR imaging system or a 3D breast tomosynthesis system. At Step 504, the clinician may review the loaded images on a display of the ultrasound imaging system and mark the images with the locations of suspected lesions via a user interface. Step 504 may be omitted when the images already include lesion markings. The clinician may input tissue properties (e.g., composition, dimensions) at Step 506, which includes, but is not limited to, identifying regions in the received images which have glandular tissue, and other regions which have fatty tissue, as well as the position of the chest wall and chest wall muscles. Alternatively, the ultrasound imaging system may automatically process the loaded images to determine the tissue properties at Step 506. At Step 508, a tissue deformation model to apply may be selected. For example, if the loaded images were acquired by an MR imaging system, a prone to supine deformation model may be selected. In some embodiments of the disclosure, a clinician may select the tissue deformation model to apply. In some other embodiments of the disclosure, the tissue deformation model to apply may be selected automatically by the ultrasound imaging system.

After the ultrasound imaging system applies the deformation model, the clinician may view visual indications of predicted lesion locations at Step 510. In some embodiments, the predicted lesion locations may be provided on a display including a lesion location interface. At Step 512, the clinician may acquire one or more ultrasound images with an ultrasound probe. The location where the clinician acquires the images may be based, at least in part, on the predicted lesion locations provided on the display. When a lesion is found, the clinician may annotate the ultrasound image to indicate the actual lesion location at Step 514. In some embodiments, the clinician may save the image and/or annotation. In some embodiments, the image and/or annotation may automatically be saved. If desired, at Step 516, the clinician may make measurements (e.g., dimensions, properties) on the lesion and/or add additional annotations. In some embodiments, the clinician may biopsy the lesion. The biopsy may be guided by the ultrasound images. If multiple lesions were detected in the previously acquired images, Steps 510-516 may be repeated for each lesion.

Figure 6:
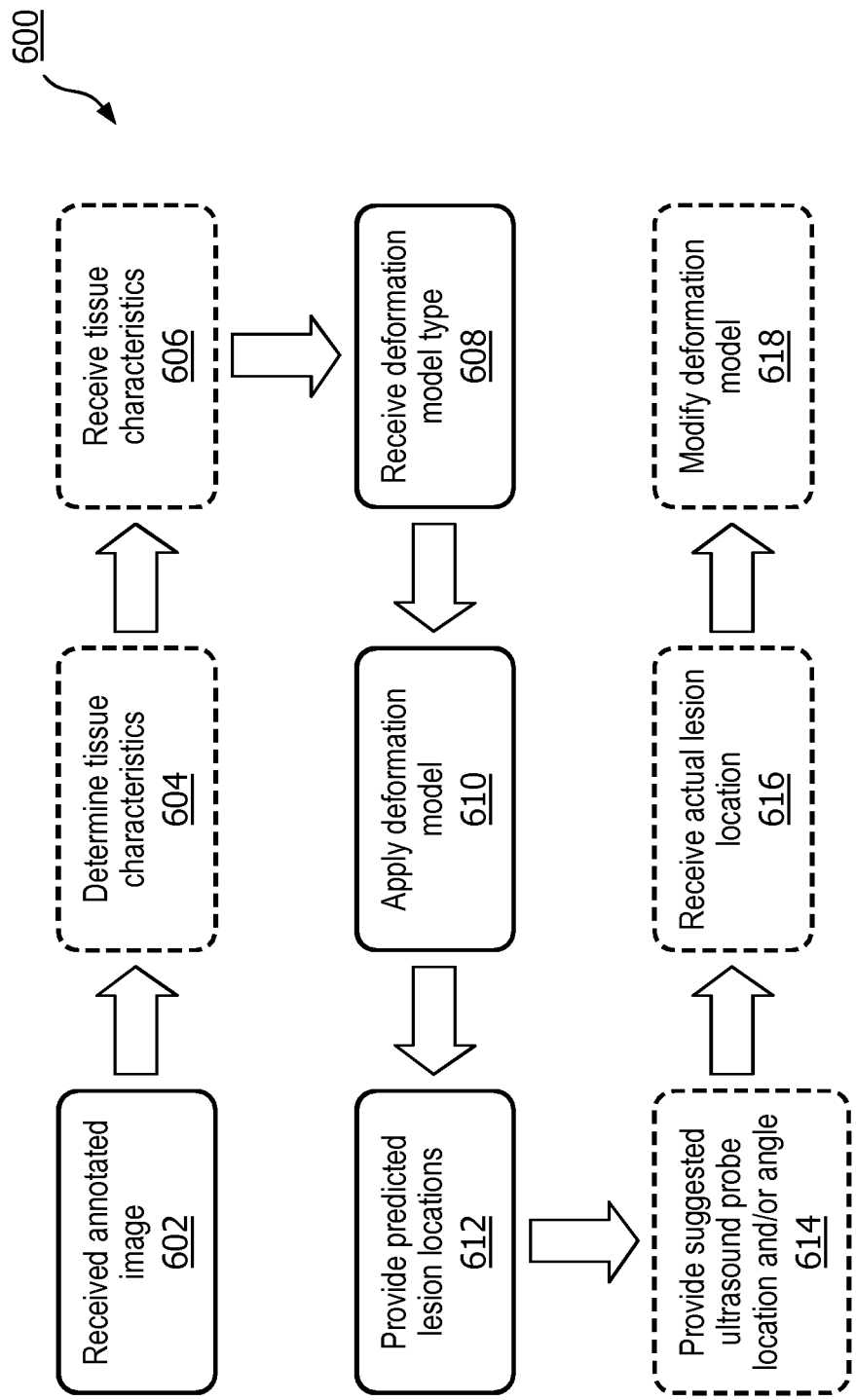
FIG. 6 is a flowchart of a process for determining predicted locations of lesions in accordance with principles of the present disclosure.

FIG. 6 is a flowchart 600 of a process for determining predicted locations of lesions in accordance with principles of the present disclosure. The process illustrated in FIG. 6 may be performed by a processor (e.g., processor 140) in some embodiments. Instructions for performing the process in flowchart 600 may be stored as processor-executable instructions in a memory accessible to a processor in some embodiments. At Step 602, one or more annotated images and/or image data may be received. The received images may correspond to previously acquired images. The annotations may include lesion location information. The previously acquired images may have been acquired by another imaging system.

At Step 604, the images may be segmented and/or otherwise processed to extract tissue characteristics (e.g., size, composition). Alternatively, at Step 606, tissue characteristics may be received, for example, as provided by a clinician via a user input device. In some embodiments, both Step 604 and 606 may be performed. That is, some tissue characteristics may be determined by analyzing the images whereas other tissue characteristics are received. At Step 608, a tissue deformation model type may be received. The deformation model type may indicate what deformation model to apply (e.g., prone to supine). In some embodiments, the deformation model type may be provided by a clinician via the user input device. In other embodiments, the deformation model type may be determined based upon acquisition information stored with the received images. Although Steps 604, 606, and 608 are shown in sequence, they could be performed in a different order or simultaneously. For example, Step 608 may be performed before Step 604.

At Step 610, a tissue deformation model may be applied to the received images to determine predicted lesion locations. The tissue deformation model may be a breast deformation model in some embodiments. Deformation models that may be used include, but are not limited to, the examples provided in reference to FIG. 1 (e.g., U.S. patent application Ser. Nos. 13/666,600 and 14/000,068). The predicted lesion locations determined by the deformation model may correspond to where the lesions may be located during an ultrasound exam. At Step 612, the predicted lesion locations may be provided to a lesion location interface, a memory, a display, a graphics processor, an image processor, and/or a combination thereof. At Step 614, a suggested ultrasound probe location and/or angle may be provided. The suggested location and/or angle may be based, at least in part, on the predicted lesion locations. In some embodiments, Step 614 may be omitted.

Optionally, at Step 616, an actual lesion location may be received. The actual lesion location may be input by the clinician based on an ultrasound image acquired with the ultrasound imaging system. At Step 618, the deformation model applied at Step 610 may be modified based, at least in part, on the actual lesion location. Modifying the deformation model based on the actual lesion location may improve accuracy of the deformation model. In some embodiments, the deformation model may be modified only when the actual lesion location is outside a predicted location and/or is more than a threshold distance away from the predicted lesion location (e.g., over 100 mm, over 500 mm, over 1 cm). The threshold distance may be set by the deformation model and/or the clinician. After Step 618, the deformation model may be reapplied to the existing data and/or the deformation model may be modified for future ultrasound exams.

Figure 7:
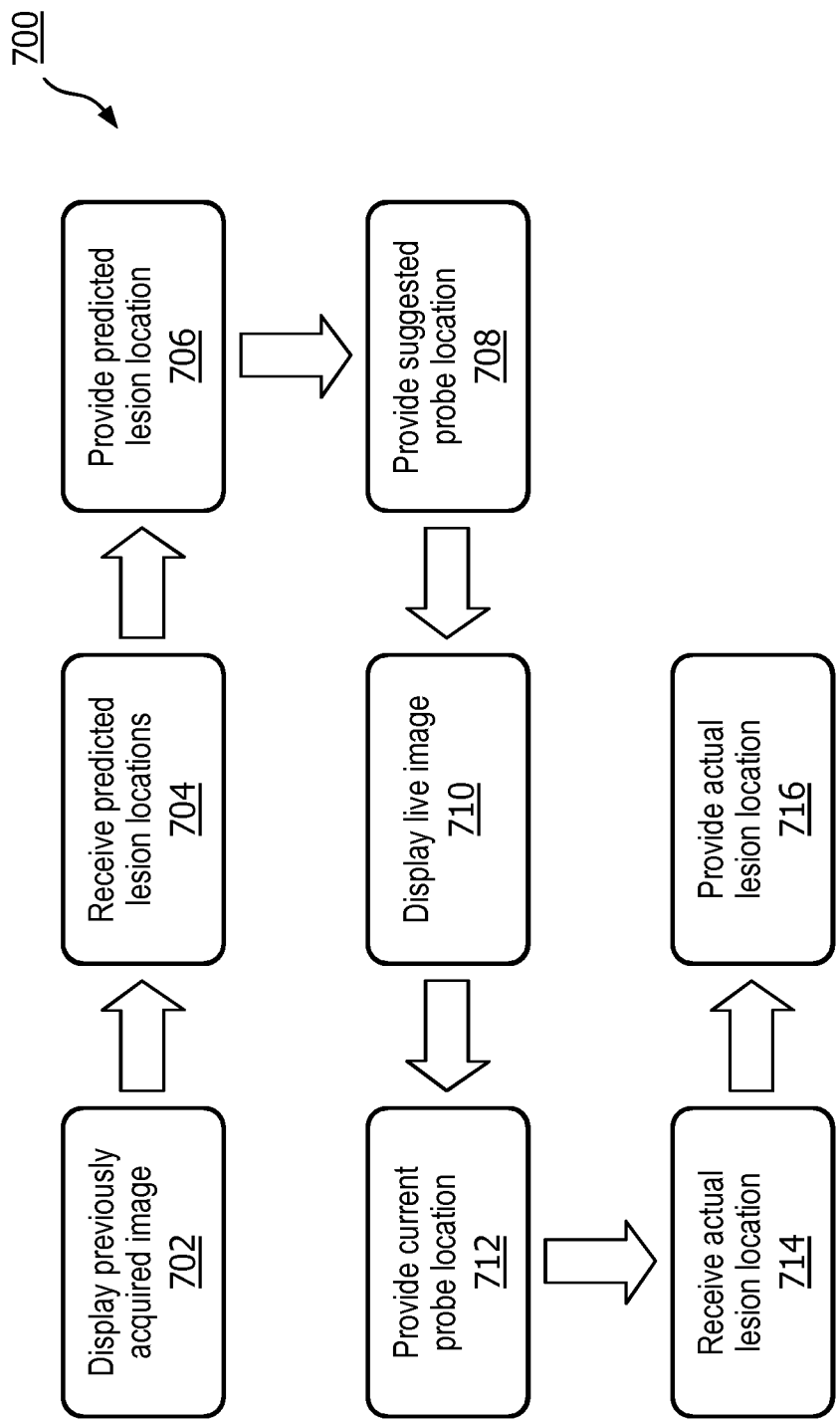
FIG. 7 is a flowchart of a process for providing visual indications of lesion locations on an ultrasound imaging system in accordance with principles of the present disclosure.

FIG. 7 is a flowchart of a process 700 for providing visual indications of lesion locations on an ultrasound imaging system in accordance with principles of the present disclosure. In some embodiments, the process 700 may be performed, at least in part, by a lesion location interface (e.g., lesion location interface 224). At Step 702, a previously acquired image may be displayed. Displaying the previously acquired image may allow a clinician to mark the image with lesion locations and/or other information. In some embodiments, the previously acquired image already includes lesion markings. A clinician may choose not to display the previously acquired image. At Step 704, predicted lesion locations may be received. The predicted lesion locations may be received from a processor configured to perform a tissue deformation model in some embodiments. At Step 706, a visual indication of the predicted lesion location may be provided. For example, the predicted lesion location may be provided as a circular or ellipsoidal graphic on a body mark as shown in FIGS. 2-4. At Step 708, a visual indication of a suggested ultrasound probe location and/or angle may be provided. For example, the suggested location and/or angle may be provided as a line drawing on a body mark as shown in FIGS. 2-4. In some embodiments, Step 708 may be omitted.

At Step 710, a live image may be displayed. The live image may be acquired by an ultrasound probe of an ultrasound imaging system. Although Step 710 is shown after Steps 702-708, Step 710 may be performed prior to and/or concurrently with Steps 702-708. At Step 712, a visual indication the current probe location and/or angle may be provided. For example, the current location and/or angle may be provided as an annotation on a body mark as shown in FIGS. 2-4. Although Step 712 is shown after Steps 702-710, Step 712 may be performed prior to and/or concurrently with Steps 702-710.

At Step 714, an actual lesion location may be received. The actual lesion location may be received via a user input device (e.g., keyboard, touch screen). The actual lesion location may be associated with an ultrasound image and/or frame of a cineloop. The actual lesion location and/or image may be stored in a memory of the ultrasound imaging system in some embodiments. At Step 716, a visual indication of the actual lesion location may be provided. For example, the actual lesion location may be provided as an annotation on a body mark as shown in FIG. 4.

As described herein, lesions found in images acquired by another imaging modality (e.g., MR, x-ray) may be more quickly and/or accurately located by applying a tissue deformation model to the images and lesion locations provided by the other imaging modality and providing visual indications of predicted lesion locations to a clinician during an ultrasound exam.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the disclosure. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system has been described with reference to MR and ultrasound imaging systems, the present system may be extended to other imaging techniques. Further, the present system may also include one or more elements which may be used with non-ultrasound imaging systems with or without real-time imaging components so that they may provide features and advantages of the present system.

It will be understood that any one of the examples, embodiments or processes described herein may be combined with one or more other examples, embodiments and/or processes or be separated and/or performed amongst separate devices or device portions in accordance with the present systems, devices and methods. Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A system comprising:
a user interface comprising a display and a user input device;
a memory operatively coupled to the user interface; and
a processor operatively connected to the user interface and the memory;
wherein the memory comprises processor-executable instructions, which can be executed by the processor, to:
receive first imaging data acquired by imaging tissue using a first imaging modality;
receive, at the user interface, an indication of a suspected location of a lesion within the imaged tissue in relation to the received first imaging data acquired by imaging the tissue using the first imaging modality;
select a deformation model based on the received first imaging data;
apply the selected deformation model to the suspected location of the lesion to generate a predicted location of the lesion when imaging the tissue using a second imaging modality, wherein the deformation model takes into account a difference in deformation of the tissue between the first imaging modality and the second imaging modality, the second imaging modality being ultrasound;
provide, at the display of the user interface, a visual indication of the predicted location of the lesion when imaging using the second imaging modality and a visual indication of a suggested position of an ultrasound probe for imaging the lesion using the second imaging modality;
define a region within which the predicted location of the lesion is located when imaging the tissue using the second imaging modality;
receive, via the user input device, an indication of an actual lesion location in second imaging data acquired by the second imaging modality;
determine if the actual lesion location when imaging the tissue using the second imaging modality is outside the region based on the indication of the actual lesion location received via the user input device; and
modify the deformation model based, at least in part, on the actual lesion location only if the actual lesion location is determined to be outside the region.

2. The system of claim 1, wherein the visual indication of the predicted location is provided by displaying a visual indication of the region.

3. The system of claim 1, wherein the processor-executable instructions further cause the user interface to provide a visual indication of a current location of an ultrasound probe in relation to an anatomical landmark, to the suggested position of the ultrasound probe, or both.

4. The system of claim 1, wherein the processor-executable instructions are further configured to cause the user interface to display an image generated from the received first imaging data.

5. The system of claim 4, wherein the received first imaging data comprises imaging data acquired by a magnetic resonance imaging system.

6. The system of claim 1, wherein the visual indication of the predicted lesion location is a graphic overlaid on a body mark.

7. The system of claim 6, wherein a graphical indication of the suggested position of the ultrasound probe is overlaid on the body mark.

8. The system of claim 1, wherein the imaging data is stored in the memory.

9. The system of claim 1, wherein processor determines if the actual lesion location is outside the region in part by determining if the actual lesion location is more than a predetermined distance away from the predicted location.

10. The system of claim 1, wherein the processor-executable instructions cause the processor to concurrently cause display, during an exam, of the received first imaging data, the visual indication of the predicted location of the lesion and the visual indication of the suggested position of the ultrasound probe, and a live ultrasound image acquired using the system.

11. The system of claim 10, wherein the processor-executable instructions cause the processor to:
receive, during the exam, a user-defined marking on the received imaging data acquired using the first imaging modality, wherein the user-defined marking indicates a revised suspected location of the lesion; and
update the visual indication of the predicted location of the lesion when imaging the tissue with the second imaging modality based on the revised suspected location of the lesion.

12. The system of claim 1, wherein the processor-executable instructions cause the processor to:
track a position of the ultrasound probe; and
retrieve for display a corresponding received image of the received first imaging data acquired using the first imaging modality based on the position of the ultrasound probe.

13. A method comprising:
receiving first imaging data acquired by imaging tissue using a first imaging modality;
receiving, via a user input device of a user interface, an indication of a suspected location of a lesion within the imaged tissue in relation to the received first imaging data acquired by imaging the tissue using the first imaging modality;
selecting a deformation model based on the received first imaging data;
applying the selected deformation model to the suspected location of the lesion to generate a predicted location of the lesion when imaging the tissue using a second imaging modality, wherein the deformation model takes into account a difference in deformation of the tissue between the first imaging modality and the second imaging modality, the second imaging modality being ultrasound;
providing, at the user interface, a visual indication of the predicted location of the lesion when imaging using the second imaging modality and a visual indication of a suggested position of an ultrasound probe for imaging the lesion using the second imaging modality;
defining a region within which the predicted location of the lesion is located when imaging the tissue using the second imaging modality;
receiving, via the user input device, an indication of an actual lesion location in second imaging data acquired by the second imaging modality;
determining if the actual lesion location when imaging the tissue using the second imaging modality is outside the region based on the indication of the actual lesion location received via the user input device; and
modifying the deformation model based, at least in part, on the actual lesion location only if the actual lesion location is determined to be outside the region.

14. The method of claim 13, further comprising analyzing the received first imaging data to determine a tissue characteristic or receiving the tissue characteristic from a user input device.

15. The method of claim 13, wherein the visual indication of the predicted location is provided by displaying a visual indication of the region.

16. The method of claim 13, wherein the determining if the actual lesion location is outside the region comprises determining if the actual lesion location is more than a predetermined distance away from the predicted location.

17. The method of claim 13, wherein the deformation model is configured to approximate displacement of breast tissue imaged in a prone positon to breast tissue being imaged in a supine position.

18. A non-transitory computer-readable medium comprising processor-executable instructions for predicting lesion locations on a system, which when executed cause the system to:
receive first imaging data acquired by imaging tissue using a first imaging modality;
receive, via a user input device of a user interface, an indication of a suspected location of a lesion within the imaged tissue in relation to the received first imaging data acquired by imaging the tissue using the first imaging modality;
select a deformation model based on the received first imaging data;
apply the selected deformation model to the suspected location of the lesion to generate a predicted location of the lesion when imaging the tissue using a second imaging modality, wherein the deformation model takes into account a difference in deformation of the tissue between the first imaging modality and the second imaging modality, the second imaging modality being ultrasound;
provide, at the user interface, a visual indication of the predicted location of the lesion when imaging using the second imaging modality and a visual indication of a suggested position of an ultrasound probe for imaging the lesion using the second imaging modality;
a region within which the predicted location of the lesion is located when imaging the tissue using the second imaging modality;

receive, via the user input device, an indication of an actual lesion location in second imaging data acquired by the second imaging modality;

determine if the actual lesion location when imaging the tissue using the second imaging modality is outside the region based on the indication of the actual lesion location received via the user input device; and modify the deformation model based, at least in part, on the actual lesion location only if the actual lesion location is determined to be outside the region.

19. The non-transitory computer readable medium comprising processor executable instructions of claim 18, which when executed further cause the system to acquire a live ultrasound image and display the live ultrasound image.

\* \* \* \* \*